(12) United States Patent
Li et al.

(10) Patent No.: US 7,781,044 B2
(45) Date of Patent: Aug. 24, 2010

(54) ORGANIC COMPOUND FOR RECORDING LAYER FOR HIGH SPEED RECORDING OF INFORMATION AND OPTICAL RECORDING MEDIUM INCLUDING THE SAME

(75) Inventors: Ming-Chia Li, Taichung County (TW); An-Tse Lee, Taipei County (TW); Chien-Liang Huang, Taoyuan County (TW); Chung-Ta Cheng, Taipei County (TW); Kuo-Chi Chiu, Hsinchu County (TW); Tzuan-Ren Jeng, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 278 days.

(21) Appl. No.: 11/850,669
(22) Filed: Sep. 5, 2007

(65) Prior Publication Data
US 2009/0061143 A1   Mar. 5, 2009

(51) Int. Cl.
B32B 3/02 (2006.01)
G11B 7/247 (2006.01)
G11B 7/249 (2006.01)
G11B 7/246 (2006.01)
C09B 45/14 (2006.01)
C09B 45/24 (2006.01)
C09B 29/00 (2006.01)
C09B 35/02 (2006.01)
C07D 265/12 (2006.01)
C07D 239/70 (2006.01)
C07D 319/08 (2006.01)

(52) U.S. Cl. ............ 428/64.8; 428/64.9; 428/65.1; 428/913; 430/270.15; 430/270.16; 430/270.18; 430/270.2; 430/945; 534/692; 534/709; 534/758; 534/838; 544/71; 544/231; 549/265; 549/331; 549/333; G9B/7.149; G9B/7.152; G9B/7.155

(58) Field of Classification Search ............ 428/64.4, 428/64.8, 64.9, 65.1, 913; 430/270.18, 270.15, 430/270.16, 270.2, 945; 534/709, 758, 774, 534/692, 816, 831, 838; 544/71, 231; 549/265, 549/330, 331, 333; G9B/7.149, 7.152, 7.155
See application file for complete search history.

(56) References Cited

U.S. PATENT DOCUMENTS 3,440,052 A * 4/1969 Heseltine .................... 430/578

(Continued)

FOREIGN PATENT DOCUMENTS

JP   2006116720 A * 5/2006

OTHER PUBLICATIONS

STN search of generic oxonol type structure prepared on Nov. 9, 2009. STN1.pdf.*

(Continued)

*Primary Examiner*—Mark Ruthkosky
*Assistant Examiner*—Gerard T Higgins
(74) *Attorney, Agent, or Firm*—Jianq Chyun IP Office (57) ABSTRACT

A recording layer including a novel organic compound for a high density optical recording medium is provided. The information may be recorded on the recording layer at a 2× speed or higher speed with a relatively lower writing power so that heat distribution of the recording layer in the irradiated area is not likely to become steep both in time and space. The organic compound incorporated in the recording layer has the following general chemical structural formula (I).

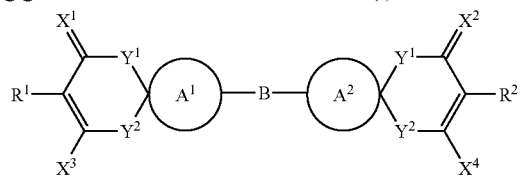

18 Claims, 3 Drawing Sheets

U.S. PATENT DOCUMENTS

| | | | |
|---|---|---|---|
| 7,238,461 B2 * | 7/2007 | Akiba et al. | 430/270.18 |
| 2003/0003396 A1 * | 1/2003 | Berneth et al. | 430/270.18 |
| 2004/0086803 A1 * | 5/2004 | Takizawa et al. | 430/270.18 |
| 2005/0063292 A1 * | 3/2005 | Shibata | 369/275.4 |
| 2006/0286338 A1 * | 12/2006 | Akiba et al. | 428/64.4 |
| 2007/0020562 A1 * | 1/2007 | Akiba et al. | 430/270.18 |

OTHER PUBLICATIONS

STN search of cyclic alkyl with oxonol moiety prepared on Nov. 9, 2009. STN2.pdf.*

STN search of specific double cyclic alkyl linked oxonol moiety prepared on Nov. 9, 2009. STN3.pdf.*

* cited by examiner

ORGANIC COMPOUND FOR RECORDING LAYER FOR HIGH SPEED RECORDING OF INFORMATION AND OPTICAL RECORDING MEDIUM INCLUDING THE SAME

BACKGROUND OF THE INVENTION

1. Field of the Invention

The present invention generally relates to an optical recording medium. More particularly, the present invention relates to an organic compound for a recording layer for high speed recording and an optical recording medium including the same.

2. Description of Related Art

In recent years, development of optical recording media employing laser have been remarkable. An example of the optical recording medium, such as an optical disc, is generally designed to irradiate a focused laser beam of about 1 μm to a thin recording layer formed on a disc shaped substrate to conduct information recording. The recording is implemented in a manner that upon absorption of the laser beam energy, the irradiated portion of the recording layer undergoes a thermal deformation such as decomposition, evaporation or melting. Reading the difference in the reflectance between the portion having a deformation formed by the laser beam and the portion without such deformation carries out reproduction of the recorded information.

Accordingly, an optical recording medium is required to efficiently absorb the energy of the laser beam, and is also required to have a predetermined amount of absorbed light to a laser beam having a specific wavelength employed for recording and to be high in the reflectance to laser beam having a specific wavelength employed for reproduction for accurately conducting the reproduction of information.

However, storage capacity of the optical recording medium employing the laser source is limited due to optical diffraction. At present, some principles and methods of enhancement of the storage density of the optical information storage media are being set forth, including such as shifting of the wavelength of the laser source, for example, from red laser to blue laser, or enhancement of the objective numerical aperture ("NA") of optical lens. Some other methods include improvement of the encoding methods of the digital signal, or a disc storage method using an extra-fine resolution near field optical structure, or a technology for increasing the storage capacity of the information storage media (e.g., a compact disc) by using stacked multiple recording layers, i.e., the recording layers of the information storage media is developed into a three dimensional space multilayer structure, to increase the storage capacity. All the methods described above may be employed to effectively increase the storage capacity of the optical recording medium.

In the method of the shifting to shorter wavelength laser source, a new generation of a high density disc storage specification (BLU-RAY DISC®) is published in 2002 by companies such as Hitachi, LG, National, Pioneer, Philips, Samsung, Sharp, Sony and Thomson Multimedia in common. A single-side BLU-RAY DISC® may be promoted up to 27 GB by employing a 405 nm blue laser source and a 0.1 mm optical transmission cover layer structure. Thus, optical recording medium employing a short wavelength laser source for reading and storage operations has become the main stream of the development.

In addition, high speed recording of information is limited due to requiring high writing power, which would generate excess heat. However, when recording is implemented at a high speed (a high linear velocity) by employing high writing power using a laser beam, heat distribution of the recording layer in an irradiated area is likely to become rapidly high resulting in a possibility that the cross-talk phenomenon becomes more pronounced or worse adversely affecting the quality of the signal.

SUMMARY OF THE INVENTION

Accordingly, the present invention is directed to an organic compound suitable for a recording layer that allows recording of information at a high speed at a lower writing power such that good write characteristics and the compatibility with the write-once recording medium may be retained.

The present invention is also directed to an optical storage medium including the recording layer comprising the organic compound that stores information recorded at a high-speed such that good write characteristics and the compatibility with the write-once recording medium may be retained when high-speed recording is performed.

According to an embodiment of the present invention, the organic compound comprises the following general chemical structural formula:

wherein $A^1$ and $A^2$, each independently represents a substituted or a non-substituted cyclic alkyl group, B represents a single bond, an oxygen atom, a $SO_2$ or a $CQ^1Q^2$, wherein $Q^1$ and $Q^2$, each independently represents a hydrogen atom, a $C_1$-$C_{18}$ alkyl group, a $C_3$-$C_{10}$ cyclo alkyl group or a phenyl group; $X^1$ and $X^2$, each independently represents an oxygen atom or a $C(CN)_2$; $X^3$ and $X^4$, each independently represents an oxygen atom posing one negative charge or OH group or a $C(CN)_2$; $Y^1$ and $Y^2$, each independently represents an oxygen atom, a $CH_2$, alkyl group or a N—$R^7$, wherein $R^7$ represents a hydrogen atom, a substituted or a non-substituted alkyl group with carbon number 1-18 ($C_{1-18}$), a substituted or a non-substituted alkoxy group with carbon number 1-18 ($C_{1-18}$), a substituted or a non-substituted carboxyl group with carbon number 1-18 ($C_{1-18}$), a substituted or a non-substituted alkyl ester group with carbon number 1-18 ($C_{1-18}$), a substituted or a non-substituted arylester, adamantyl carbonyl group or an adamantyl group, a substituted or a non-substituted aralkyl group; and $R^1$ and $R^2$, each independently comprises hydrogen atom(s) or an azo group or a substituted polymethine group or a non-substituted polymethine group.

According to an embodiment of the present invention, the information may be recorded on the recording layer comprising the organic compound at a 2× speed (linear velocity of 13.22 m/s) or higher speed with a relatively lower writing power so that heat distribution of the recording layer in the irradiated area may be maintained at an optimal level, and heat distribution may not likely become rapidly high, and therefore good write characteristics of the write-once medium may be ensured and the compatibility with the write-once storage medium may be retained.

According to an embodiment of the present invention, the organic compound shows absorption at wavelength within a range of 300 to 600 nm, and is excellent in the thermal stability.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE INVENTION

It is to be understood that both the foregoing general description and the following detailed description are exemplary, and are intended to provide further explanation of the invention as claimed.

The present invention provides an organic compound for a recording layer suitable for implementing high speed recording of information thereon by employing short wavelength laser source, and reproduction/playback of the recorded information recordings. The organic compound comprises the following general chemical structural formula:

(I)

wherein $A^1$ and $A^2$, each independently represents a substituted or a non-substituted cyclic alkyl group, B represents a single bond, an oxygen atom, a $SO_2$ or a $CQ^1Q^2$, wherein $Q^1$ and $Q^2$, each independently represents a hydrogen atom, a $C_1$-$C_{18}$ alkyl group, a $C_3$-$C_{10}$ cyclo alkyl group, or a phenyl group; $X^1$ and $X^2$, each independently represents an oxygen atom or a $C(CN)_2$; $X^3$ and $X^4$, each independently represents an oxygen atom posing one negative charge or OH group or a $C(CN)_2$; $Y^1$ and $Y^2$, each independently represents an oxygen atom, a $CH_2$, alkyl group or a N—$R^7$, wherein $R^7$ represents a hydrogen atom, a substituted or a non-substituted alkyl group with carbon number 1-18 ($C_{1-18}$), a substituted or a non-substituted alkoxy group with carbon number 1-18 ($C_{1-18}$), a substituted or a non-substituted carboxyl group with carbon number 1-18 ($C_{1-18}$), a substituted or a non-substituted alkyl ester group with carbon number 1-18 ($C_{1-18}$), a substituted or a non-substituted arylester, adamantyl carbonyl group or an adamantyl group, or a substituted or a non-substituted aralkyl group; and $R^1$ and $R^2$, each independently comprises hydrogen atom(s) or an azo group or a substituted polymethine group or a non-substituted polymethine group.

According to an embodiment of the present invention, when the $X^1$ and $X^2$, each independently represents an oxygen atom or a $C(CN)_2$; $X^3$ and $X^4$, each independently represents an oxygen or a $C(CN)_2$, the organic compound comprises the following isomer chemical structural formula.

(II)

According to an embodiment of the present invention, when $R^1$ and $R^2$, each independently comprises a substituted polymethine group or a non-substituted polymethine group, the organic compound comprises the following chemical structural formula:

(Ia)

wherein m and n represent an integer including 0 or 1; $R^3$ and $R^4$, each independently represents a substituted or non-substituted alkyl group with carbon number 1-18 ($C_{1-18}$), a substituted or non-substituted alkoxy group with carbon number 1-18 ($C_{1-18}$), a substituted or non-substituted carboxyl group with carbon number 1-18 ($C_{1-18}$), a substituted or non-substituted alkyl ester group with carbon number 1-18 ($C_{1-18}$), a substituted or non-substituted arylester, adamantyl carbonyl group, adamantyl group, or substituted or non-substituted aralkyl group; $Z^1$ and $Z^2$, each independently represents a substituted or non-substituted organic cyclic group, and a heterocyclic ring containing oxygen atom, sulfur atom, selenium atom, nitrogen atom or benzene cyclic group; $L^1, L^2, L^3, L^4, L^5, L^6, L^7$ and $L^8$, each independently represents a substituted or a non-substituted methine group.

According to an embodiment of the present invention, when $R^1$ and $R^2$ comprise an azo group, the organic compound comprises the following chemical structural formula:

(Ib)

wherein $R^5$ and $R^6$, each independently represents a substituted or a non-substituted organic cyclic group, a heterocyclic ring containing an oxygen atom, a sulfur atom, a selenium atom, a nitrogen atom or a benzene cyclic group.

According to another embodiment of the present invention, $R^1$ comprises a polymethine group and $R^2$ comprises an azo group.

Following are some of the specific derivatives of the organic compound (I)˜(Ia)˜(Ib) of the present invention. However, these examples are not intended to limit the scope of the present invention as such.

(I-01)

(I-02)

(I-03)

(I-04)

(I-05)

(I-06)

(I-07)

-continued (I-08)

(I-09)

(I-10)

(I-11)

(Ia-01)

(Ia-02)

(Ia-03)

(Ia-04)

(Ia-05)

(Ia-06)

-continued (Ib-01)

(Ib-02)

(Ib-03)

(Ib-04)

(Ib-05)

-continued (Ib-06)

(Iab-01)

(Iab-02)

According to the specific derivatives of the organic compound expressed in (Ib-05) and (Ib-06), when $R^1$ and $R^2$ comprise an azo group or $R^1$ comprises a polymethine group and $R^2$ comprises an azo group, the organic compound is complexed with a divalent metal to form the metal azo complex, and wherein the divalent metal comprises Fe, Co, Cu, Ni, Mg Al, Pt, Pd, Cr, Mn, or Zn.

Hereinafter, an example synthesis process of the organic compound (I-04) is described as follows.

A mixture of 10.0 g of 2,2-Bis(4-oxocyclohexyl)propane, 8.81 g of Malonic acid and 50.0 g of Acetic anhydride was gradually admix with 4.0 g of $H_2SO_4$ at room temperature. After 24 hours of reaction at room temperature, the reaction mixture was filtered under suction to obtain a white precipitate. The precipitate was washed with water, dried and weighed. The reaction yield was 15.0 g white powder of the organic compound (I-04).

Hereinafter, an example synthesis process of the organic compound (I-11) is described as follows.

Figure 2:
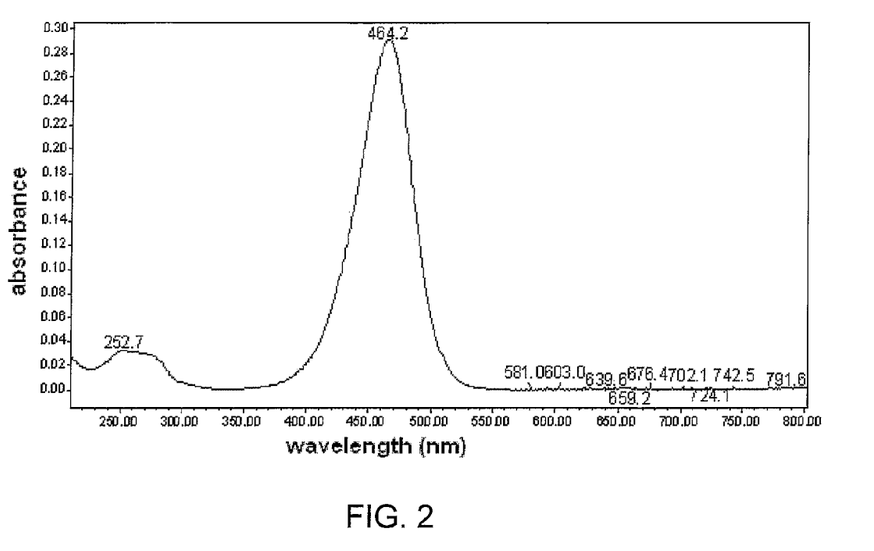
FIG. 2 illustrates an UV/Visible/IR absorption spectrum of an organic compound (I-11) of the present invention.

A mixture of 10.0 g of the organic compound (I-04) and 9.0 g of 4-(Diethylamino)benzaldehyde was gradually admix with 50.0 g of Methanol at room temperature, then the reaction mixture was heated to the reflux temperature of methanol for 8 hours. After 8 hours of reaction, the reaction mixture was filtered under suction to obtain a yellow-orange precipitate. The precipitate was washed with Methanol, dried and weighed. The reaction yield was 10.0 g yellow-orange powder of the organic compound (I-11). FIG. 2 illustrates an UV/Visible/IR absorption spectrum of the organic compound (I-11).

Hereinafter, an example synthesis process of the organic compound (Ia-01) is described as follows.

A mixture of 10.0 g of 2,3,3-Trimethylindolenine and 12.0 g of 1-Iodobutane was gradually admix with 50.0 ml of Ethyl acetate at room temperature, then the reaction mixture was heated to the reflux temperature of ethyl acetate for 12 hours. After 12 hours of reaction, the reaction mixture was filtered under suction to obtain a yellow-white precipitate. The precipitate was washed with ethyl acetate, dried and weighed. The reaction yield was 10.0 g yellow-white powder of the intermediate compound (IM-01).

(IM-01)

Next, a mixture of 10.0 g of the intermediate compound (IM-01) and 5.5 g of N,N'-Diphenylformamidine was gradually admix with 15.0 ml of acetic anhydride at room temperature, then the reaction mixture was heated to 80° C. for 12 hours. After 12 hours of reaction, the reaction mixture was cooled down to room temperature to obtain a dark-green precipitate. The precipitate was washed with ethyl acetate and dried to obtain dark-green powder of the intermediate compound (IM-02). The reaction yield was 3.0 g dark-green powder of the intermediate compound (IM-02).

(IM-02)

Figure 3:
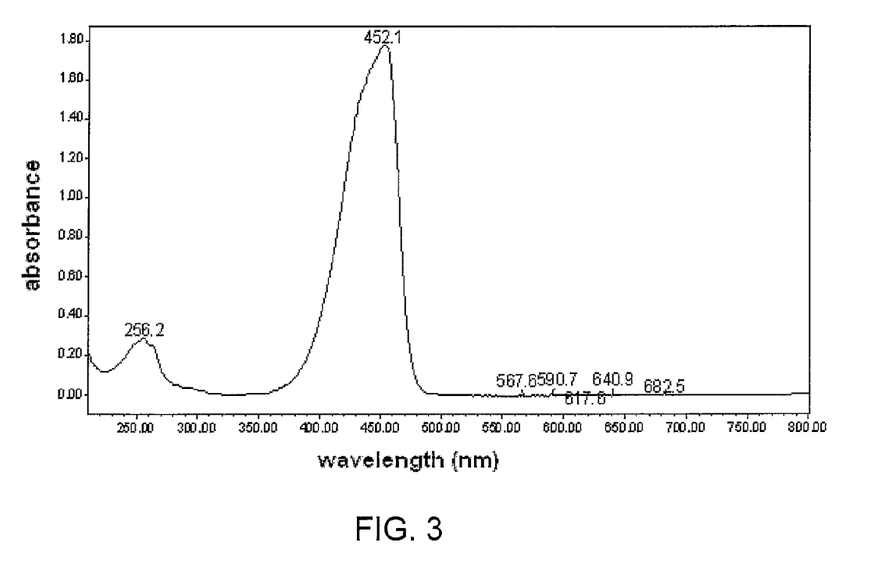
FIG. 3 illustrates UV/Visible/IR absorption spectrums of an organic compound (Ia-01) of the present invention.

Next, a mixture of 3.0 g of the intermediate compound (IM-02), 1.0 g sodium acetate and 1.3 g of the organic compound (I-04) was gradually admix with 20.0 ml of methanol at room temperature. Next, the reaction mixture was heated to the reflux temperature of methanol for 12 hours. After 12 hours of reaction, the reaction mixture was filtered under suction to obtain a yellow precipitate. The precipitate was washed with methanol and dried. The reaction yield was 2.0 g yellow powder of the organic compound (Ia-01). FIG. 3 illustrates an UV/Visible/IR absorption spectrums of the organic compound (Ia-01).

Hereinafter, an example synthesis process of the organic compound (Ib-02) is described as follows.

Figure 4:
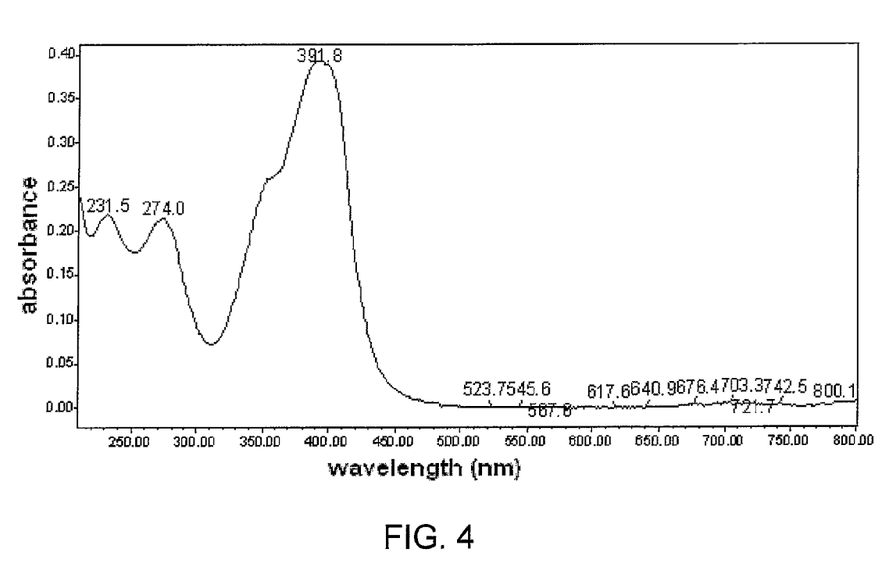
FIG. 4 illustrates an UV/Visible/IR absorption spectrum of an organic compound (Ib-02) of the present invention.

A mixture of 5.0 g of 4-Aminoantipyrine, 50 ml of water and 8.0 g of HCl was gradually admix with 8 g of $NaNO_2$ (35% w/w) aqueous solution at 0° C. for 1.5 hours. Next, the diazotized mixture was added dropwise to the solution of 5.0 g of the organic compound (I-04) in 100 ml of water and 8.5 g of $Na_2CO_3$. The reaction mixture was stirred at the room temperature. After 2 hours, the reaction mixture was filtered under suction to obtain a yellow precipitate. The precipitate was washed with methanol and dried. The reaction yield was 2.0 g yellow powder of the organic compound (Ib-02). FIG. 4 illustrates an UV/Visible/IR absorption spectrum of the organic compound (Ib-02).

Information may be recorded on the recording layer comprising the organic compound at a 2× speed (linear velocity of 13.22 m/s) or a higher speed with a relatively lower writing power such that heat distribution of the recording layer in the irradiated area may be maintained at an optimal level, and may not likely become rapidly high, and therefore good write characteristics and the compatibility with the write-once storage medium may be retained. Thus, the recording layer incorporated with the organic compound (I), (Ia), (Ib) and (Iab) of the present invention makes high speed recording of the information thereon using a lower writing power possible.

Figure 1:
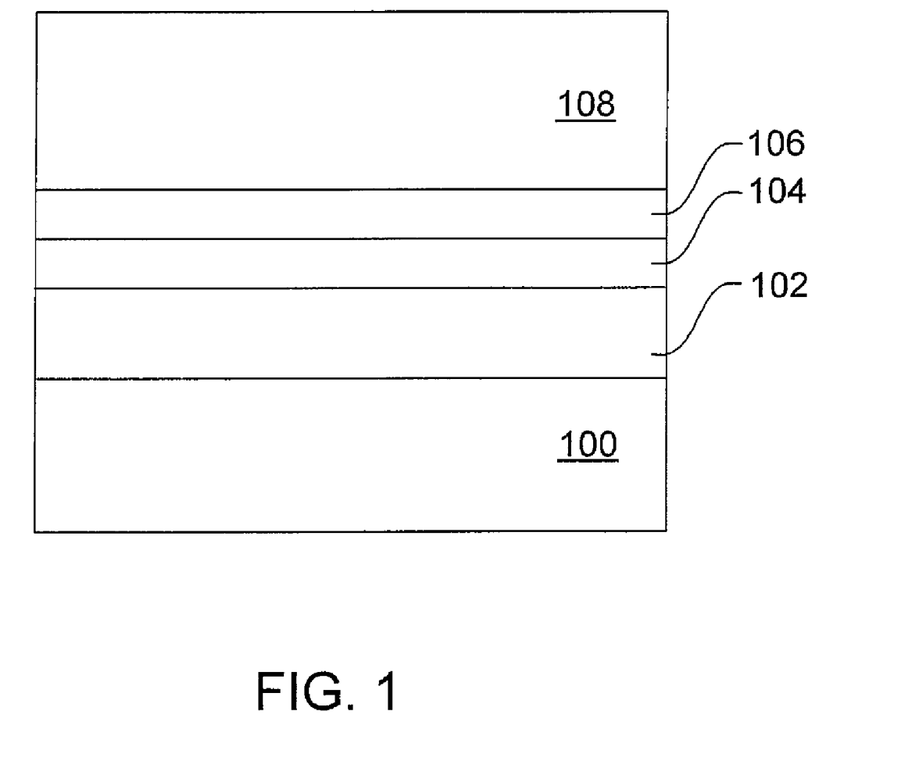
FIG. 1 illustrates a cross sectional view of a high density optical recording medium according to an embodiment of the present invention.

Hereinafter, a structure of a blue-ray high density optical recording medium will be described with reference to FIG. 1 as follows. Referring to FIG. 1, the high density optical recording medium comprises a first substrate 100, a cover layer 108 and at least a recording layer 102, containing the organic compound (I) of the present invention described above, disposed between the first substrate 100 and the cover layer 108. Furthermore, a reflective layer 106 may be provided on the recording layer 102 and also, if necessary, a primer coating layer may be provided on the first substrate 100, a protective layer 104 may be provided on the recording layer 102 or the reflective layer 106, and a surface protective layer 104 may be provided on the first substrate 100 at the opposite side to the recording layer 102.

According to an embodiment of the present invention, the first substrate 100 and the cover layer 108 are preferably transparent to the laser beam. The material of the first substrate 100 and the cover layer 108 may be comprised of, for example but not limited to, glass or plastic materials. From various aspects, the plastic material is preferably used. The plastic material may be comprised of, for example but not limited to, polycarbonate (PC), polymethylmethacrylate (PMMA), polymer resins, glass, acryl resin, methacryl resin, vinyl acetate resin, vinyl chloride resin, nitro cellulose, polyethylene resin, polypropylene resin, polycarbonate resin, polyimide resin, epoxy resin, polysulfone resin or metallocene based cyclic olefin copolymer (mCOC). Among the plastic materials mentioned above, an injection molded polycarbonate resin substrate may of particular interest from the viewpoint of the high productivity, low cost and moisture resistance. The thickness of the first substrate 100 may be between 0.5 mm to 1.3 mm, more preferably about 0.6 mm. The first substrate 100, for example, comprises lands, or pre-curved pits or grooves with a track pitch of less than 0.4 µm. The lands, or pre-curved pits or grooves in the first substrate 100 are used to provide a signal surface for the laser tracking of the pick-up head of the laser.

According to an embodiment of the present invention, the recording layer 102 of the present invention containing the organic compound (I) is formed with a thickness in a range of about 10 Å to 500 nm, preferably in a range of about 5 nm to 200 nm. The recording layer 102 of the present invention may be formed by employing well known thin-film-forming methods such as a spin coating method, a roller press method, a vacuum vapor deposition method, a sputtering method, a doctor blade method, a casting method, inkjet printing method or a dipping method. However, the spin coating method is preferred from the viewpoint of the productivity and cost. A 1.5 Wt. % solution of the organic compound (I) of the present invention in 2,2,3,3-tetrafluoropropanol may be prepared and used for spin coating the thin film recording layer 102 over the first substrate 100. It should also be noted that other solvents such as alcohol, ketone, ether, chloroform or dichloromethane may also be used to make the dye solution for forming the thin film recording layer 102. Preferred examples of alcohol include 2,2,3,3-tetrafluoropropanol, methanol, ethanol and isopropanol. Preferred examples of ketone include acetone and dimethyl-ethyl ketone. Preferred examples of ether include ethyl ether and tetrahydrofuran.

According to an embodiment of the present invention, the reflective layer 106 may be comprised of, for example but not limited to, metals such as gold, silver, copper, aluminum, platinum, titanium or alloys thereof, or equivalents thereof, which have high reflectance in the laser wavelength region to be employed. The thickness of the reflective layer 106 may be about 1 nm to 300 nm. The reflective layer 406 may be formed on the recording layer 102 using vacuum sputtering.

Finally, the cover layer 108 may be adhered over the reflective layer 106 to complete the fabrication of the blue-ray high density optical recording medium. The cover layer 108 may be adhered over the reflective layer 106 by spin coating, screen printing, thermal gluing or roller pressing.

According to an embodiment of the present invention, the surface protective layer on the mirror surface side of the first substrate may be comprised of, for example but not limited to, an ultraviolet curable acryl resin or a silicon type hard coating agent. The surface protective layer is preferably provided with an antistatic ability for preventing dust or the like from adhering.

The recording layer 102 of the optical recording medium of the present invention may be formed on one side of the first substrate 100. According to an embodiment of the present invention, multiple recording layers 102 may be used for fabricating a multi-layer stacked optical recording medium structure with a view of further increasing the storage capacity of the optical recording medium.

High speed recording, for example at a 2× speed (linear velocity of 13.22 m/s) or higher speed, on an optical recording medium may be conducted by irradiating a laser beam, for example using a blue laser with a wavelength of 405 nm, to record information onto the recording layer with a writing power within a range of, for example 10-11 mW may be implemented. At the portion irradiated with the laser beam, a thermal deformation of the recording layer, such as decomposition, evaluation or melting may be formed due to absorption of the laser energy. Reproduction of the recorded information can be conducted by reading the difference in the reflectance between the portion having such a thermal deformation formed by a laser beam and the portion having no such a thermal deformation.

The recording characteristics of the above optical recording medium was evaluated using a PULSTEC ODU-1000 instrument under the conditions including a blue laser beam with wavelength of 405 nm, objective lens numerical aperture (NA) of 0.65, 1× speed CLV=6.61 m/s, and 2× speed CLV=13.22 m/s. Wherein PRSNR represents Partial Response Signal-to-Noise Ratio and SbER represents Simulated bit Error Rate. The recording characteristics of the above recording layers were carried out at 1× speed and 2× speed. As can be seen from the recording characteristics results shown in Tables 1 and 2 below that the optical recording medium incorporating the recording layer including, for example, the organic compound (Ia-01), (Ia-02) and (Ib-02) may be practically used to implement high-speed recording at higher speed, for example, at 2× speed. Thus, the organic dye derivatives of the present invention described above can be practically used as an optical recording material for a recording layer for, for example, implementing high-speed recording at a 2× or higher recording speed by using a lower writing power of about 10-11 mW.

TABLE 1

COMPARISON OF RECORDING CHARACTERISTICS AT 1X SPEED

| Recording Layer Including Organic Compound | Writing Power | Blue Ray Recording device feature-1 (PRSNR Spec. > 15) | Blue Ray Recording device feature-2 (SbER < 5 × $10^{-5}$) |
|---|---|---|---|
| Ia-01 | 7.5 mW | 29.5 | $3.8 \times 10^{-8}$ |
| Ia-02 | 8.0 mW | 31.5 | $3.2 \times 10^{-11}$ |
| Ib-02 | 10.25 mW | 29 | $5.9 \times 10^{-8}$ |

TABLE 2

COMPARISON OF RECORDING CHARACTERISTICS AT 2X SPEED

| Recording Layer Including Organic Compound | Writing Power | Blue Ray Recording device feature-1 (PRSNR Spec. > 15) | Blue Ray Recording device feature-1 (SbER < 5 × $10^{-5}$) |
|---|---|---|---|
| Ia-01 | 10.7 mW | 22.0 | $3.8 \times 10^{-7}$ |
| Ia-02 | 10.5 mW | 24.5 | $2.6 \times 10^{-8}$ |

Accordingly, the information may be recorded on the recording layer comprising the organic compound at a 2× speed (13.22 m/s) or higher speed at a relatively lower writing power, for example in a range of about 7 mW to 12 mW, such that heat distribution of the recording layer in the irradiated area may be maintained at an optimal level, and may not likely become rapidly high, and therefore good write characteristics and the compatibility with the write-once storage medium may be retained. Thus, the recording layer incorporated with the organic compound (I), (Ia) and (Ib) of the present invention makes high speed recording of the information thereon using a lower writing power possible.

According to an embodiment of the present invention, the organic compound shows absorption at wavelength within a range of 300 to 600 nm, and is excellent in the thermal stability.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. An organic compound comprising the following general chemical structural formula (I):

(I)

wherein $A^1$ and $A^2$, each independently represent a substituted or a non-substituted cyclic alkyl group; B represents a single bond, an oxygen atom, a $SO_2$ or a $CQ^1Q^2$, wherein $Q^1$ and $Q^2$, each independently represent a hydrogen atom, a $C_1$-$C_{18}$ alkyl group, a $C_3$-$C_{10}$ cyclo alkyl group or a phenyl group; $X^1$ and $X^2$, each independently represent an oxygen atom or a $C(CN)_2$; $X^3$ and $X^4$, each independently represent an oxygen atom posing one negative charge, an OH group or a $C(CN)_2$; $Y^1$ and $Y^2$, each independently represent an oxygen atom, a $CH_2$, an alkyl group or a N—$R^7$, wherein $R^7$ is selected from the group consisting of a hydrogen atom, a substituted or a non-substituted alkyl group with carbon number 1-18 ($C_{1-18}$), a substituted or a non-substituted alkoxy group with carbon number 1-18 ($C_{1-18}$), a substituted or a non-substituted carboxyl group with carbon number 1-18 ($C_{1-18}$), a substituted or a non-substituted arylester, an adamantyl carbonyl group, an adamantyl group, and a substituted or a non-substituted aralkyl group; and $R^1$ and $R^2$, each independently comprise a hydrogen atom, an azo group, a substituted polymethine group or a non-substituted polymethine group.

2. The organic compound according claim 1, wherein when $R^1$ and $R^2$, each independently comprise a substituted or a non-substituted polymethine group, the organic compound comprises the following general chemical structural formula (Ia):

(Ia)

wherein m and n represent an integer of 0 or 1 $R^3$ and $R^4$, each independently represent a substituted or non-substituted alkyl group with carbon number 1-18 ($C_{1-18}$), a substituted or non-substituted alkoxy group with carbon number 1-18 ($C_{1-18}$), a substituted or non-substituted carboxyl group with carbon number 1-18 ($C_{1-18}$), a substituted or non-substituted alkyl ester group with carbon number 1-18 ($C_{1-18}$), a substituted or non-substituted arylester, an adamantyl carbonyl group, an adamantyl group, or a substituted or non-substituted aralkyl group; $Z^1$ and $Z^2$ are each independently selected from the group consisting of a substituted or non-substituted alkylene group and a substituted or non-substituted alkylene group with an oxygen atom, a sulfur atom, a selenium atom, or a nitrogen atom; and $L^1$, $L^2$, $L^3$, $L^4$, $L^5$, $L^6$, $L^7$ and $L^8$, each independently represent a substituted or a non-substituted methine group.

3. The organic compound according claim 1, wherein when $R^1$ and $R^2$, each independently comprise an azo group, the organic compound comprises the following general chemical structural formula (Ib):

(Ib)

wherein $R^5$ and $R^6$, each independently represent a substituted or a non-substituted organic cyclic group, a heterocyclic ring containing an oxygen atom, a sulfur atom, a selenium atom, or a nitrogen atom or a benzene cyclic group.

4. The organic compound according claim 1, wherein $R^1$ comprises a substituted or a non-substituted polymethine group and $R^2$ comprises an azo group.

5. The organic compound according claim 3, wherein the organic compound is complexed with a divalent metal to form a metal azo complex, and wherein the divalent metal comprises Fe, Co, Cu, Ni, Mg Al, Pt, Pd, Cr, Mn, or Zn.

6. The organic compound according claim 4, wherein the organic compound is complexed with a divalent metal to form a metal azo complex, and wherein the divalent metal comprises Fe, Co, Cu, Ni, Mg Al, Pt, Pd, Cr, Mn, or Zn.

7. A high-density optical recording medium, comprising:
a first substrate and a cover layer; and
at least a recording layer, disposed between the first substrate and the cover layer, comprising at least an organic compound comprising the following general chemical structural formula (I):

(I)

wherein $A^1$ and $A^2$, each independently represent a substituted or a non-substituted cyclic alkyl group; B represents a single bond, an oxygen atom, a $SO_2$ or a $CQ^1Q^2$, wherein $Q^1$ and $Q^2$, each independently represent a hydrogen atom, a $C_1$-$C_{18}$ alkyl group, a $C_3$-$C_{10}$ cyclo alkyl group, or a phenyl group; $X^1$ and $X^2$, each independently represent an oxygen atom or a $C(CN)_2$; $X^3$ and $X^4$, each independently represent an oxygen atom posing one negative charge, an OH group or a $C(CN)_2$; $Y^1$ and $Y^2$, each independently represent an oxygen atom, a $CH_2$, or a N—$R^7$, wherein $R^7$ represents a hydrogen atom, a substituted or a non-substituted alkyl group with carbon number 1-18 ($C_{1-18}$), a substituted or a non-substituted alkoxy group with carbon number 1-18 ($C_{1-18}$), a substituted or a non-substituted carboxyl group with carbon number 1-18 ($C_{1-18}$), a substituted or a non-substituted alkyl ester group with carbon number 1-18 ($C_{1-18}$), a substituted or a non-substituted arylester, an adamantyl carbonyl group, an adamantyl group, or a substituted or a non-substituted aralkyl group; and $R^1$ and $R^2$, each independently comprise a hydrogen atom, an azo group, a substituted polymethine group or a non-substituted polymethine group.

8. The high-density optical recording medium according claim 7, wherein when $R^1$ and $R^2$, each independently comprise a substituted or a non-substituted polymethine group, the organic compound comprises the following general chemical structural formula (Ia):

(Ia)

wherein m and n represent an integer of 0 or $R^3$ and $R^4$, each independently represent a substituted or non-substituted alkyl group with carbon number 1-18 ($C_{1-18}$), a substituted or non-substituted alkoxy group with carbon number 1-18 ($C_{1-18}$), a substituted or non-substituted carboxyl group with carbon number 1-18 ($C_{1-18}$), a substituted or non-substituted alkyl ester group with carbon number 1-18 ($C_{1-18}$), a substituted or a non-substituted arylester, an adamantyl carbonyl group, an adamantyl group, or a substituted or non-substituted aralkyl group; $Z^1$ and $Z^2$ are each independently selected from the group consisting of a substituted or non-substituted alkylene group and a substituted or non-substituted alkylene group with an oxygen atom, a sulfur atom, a selenium atom, or a nitrogen atom; and $L^1$, $L^2$, $L^3$, $L^4$, $L^5$, $L^6$, $L^7$ and $L^8$, each independently represent a substituted or a non-substituted methine group.

9. The high-density optical recording medium according claim 7, wherein when $R^1$ and $R^2$ comprise an azo group, the organic compound comprises the following general chemical structural formula (Ib):

(Ib)

wherein $R^5$ and $R^6$, each independently represent a substituted or non-substituted organic cyclic group, a heterocyclic ring containing an oxygen atom, a sulfur atom, a selenium atom, or a nitrogen atom or a benzene cyclic group.

10. The high-density optical recording medium according claim 7, wherein $R^1$ comprises a substituted or non-substituted polymethine group and $R^2$ comprises an azo group.

11. The high-density optical recording medium according claim 9, wherein the organic compound is complexed with a divalent metal to form a metal azo complex, and wherein the divalent metal comprises Fe, Co, Cu, Ni, Mg Al, Pt, Pd, Cr, Mn, or Zn.

12. The high-density optical recording medium of claim 7, wherein a material of the first substrate and the cover layer is selected from the group consisting of polycarbonate (PC), polymethylmethacrylate (PMMA), polymer resins, glass, acryl resin, methacryl resin, vinyl acetate resin, vinyl chloride resin, nitro cellulose, polyethylene resin, polypropylene resin, polycarbonate resin, polyimide resin, epoxy resin, polysulfone resin and metallocene based cyclic olefin copolymer (mCOC).

13. The high-density optical recording medium of claim 7, wherein a thickness of the first substrate is between 0.5 mm to 1.3 mm.

14. The high-density optical recording medium of claim 7, wherein a thickness of the cover layer is between 0.01 mm to 0.7 mm.

15. The high-density optical recording medium of claim 7, wherein the first substrate comprises a land-and-groove surface on a single side thereof.

16. The high-density optical recording medium of claim 7, further comprising a reflective layer disposed between the cover layer and the first substrate and a material of the reflective layer is selected from the group consisting of gold, silver, copper, aluminum, platinum, titanium and alloys thereof.

17. The high-density optical recording medium of claim 16, further comprising a protective layer disposed on the recording layer or the reflective layer.

18. The high-density optical recording medium of claim 17, wherein a material of the protective layer comprises SiN, $SiO_2$, ZnS—$SiO_2$, an ultraviolet curable acryl resin or a silicon type hard coating agent.

* * * * *